United States Patent [19]

Cawthon et al.

[11] Patent Number: 4,973,723

[45] Date of Patent: Nov. 27, 1990

[54] PROCESS FOR PREPARING SILACYCLOALKANES

[75] Inventors: Garret D. Cawthon, Midland, Mich.; John J. D'Errico, Wethersfield, Conn.; William J. Schulz, Jr., Midland, Mich.

[73] Assignee: Dow Corning Corporation, Midland, Mich.

[21] Appl. No.: 531,616

[22] Filed: Jun. 1, 1990

[51] Int. Cl.$^5$ .............................................. C07F 7/08
[52] U.S. Cl. .................................................. 556/406
[58] Field of Search ........................................ 556/406

[56] References Cited

U.S. PATENT DOCUMENTS

| | | | |
|---|---|---|---|
| 2,607,791 | 8/1952 | Goodwin | 556/406 |
| 3,100,788 | 8/1963 | Jenkner | 260/448.2 |
| 3,445,495 | 5/1969 | Nelson | 556/406 X |
| 3,899,523 | 8/1975 | Seyfertle et al. | 556/406 |
| 4,328,350 | 5/1982 | Guselnikov et al. | 556/406 |
| 4,499,020 | 3/1970 | Robinson | 260/448.2 |
| 4,866,153 | 9/1989 | Bortolin et al. | 556/406 X |

OTHER PUBLICATIONS

Laane, Synthesis of Silacyclobutane and Some Related Compounds, J. Am. Chem. Soc. 89:1144, 1967.

Primary Examiner—Paul F. Shaver
Attorney, Agent, or Firm—William F. Boley

[57] ABSTRACT

The present invention is a process for reducing the content of halogen bound to the silicon atom of halosilacycloalkanes. The process employs an alkylaluminum hydride as a reducing agent. Alkylaluminum hydrides have been found to be highly effective in removing the halogen bound to silicon, with lessor affect on the reactive silacycloalkane ring. In another embodiment of the present invention, the halosilacycloalkane is added beneath the surface of an excess of liquid alkylaluminum hydride. The temperature and the pressure of the reaction are maintained such that the resultant silacycloalkane products are immediately vaporized and removed from the reaction vessel. This minimizes further reaction of products and improves the yield of desired product.

23 Claims, No Drawings

PROCESS FOR PREPARING SILACYCLOALKANES

BACKGROUND OF INVENTION

The present invention relates to a process for the preparation of silacycloalkanes. The described process uses an alkylaluminum hydride to reduce halosilacycloalkanes to silacycloalkanes. In an additional embodiment of the instant invention, the halosilacycloalkane is added to the alkylaluminum hydride and the silacycloalkane product is immediately vacuum distilled from the mixture. The process, as described, provides high yield of silacycloalkane product.

Silacycloalkanes have been found to be useful in producing hydrogenated films with a silicon and carbon backbone. These films are known to exhibit very low dark conductivity at room temperature and to show good corrosion resistance. The small, strained, organosilicon ring is known to make silacyclobutanes highly reactive, particularly with nucleophilic and electrophilic reagents. As a consequence of the unique chemistry of silacycloalkanes, few methods for their production have been reported.

Laane, J. Am. Chem. Soc. 89:1144, 1967, appears to be the first to describe a process for the preparation of silacycloalkanes. Laane prepared 1,1-dichloro-1-silacyclobutane by adding 3-chloropropyltrichlorosilane dropwise to ethyl ether, containing magnesium powder. The 1,1-dichloro-1-silacyclobutane, in n-butyl ether, was added dropwise to lithium aluminum hydride, in n-butyl ether, to form the reduced silacyclobutane. The addition was completed over a five-hour period, with the reaction mixture maintained at a temperature of $-5°$ C. to $+5°$ C. After 10 hours, the reaction was allowed to progress at room temperature and after 24 hours the mixture was distilled. The reported yield of product was 46%.

Silicon-hydrogen compounds can be prepared by reduction of silicon halides, partially halogenated silanes, or organohalogen silanes, in the presence of metal catalysts, such as aluminum, magnesium, and the like. The use of hydrides such as $LiAlH_4$ or $AlH_3$, has also been proposed for this purpose. Jenker, U.S. Pat. No. 3,100,788, issued Aug. 13, 1963, described a process for adding hydrogen to halogenated organosilanes by employing an alkali metal or alkali hydride in a hydrogen atmosphere.

Robinson, U.S. Pat. No. 3,499,020, issued Mar. 3, 1970, describes a process for reducing compounds of the type "$R_nSiX_{4-n}$, where R is hydrogen, alkyl, cycloalkyl, alkenyl, aryl, or alkaryl and X is halogen, $-NR'_2$, or an oxygen-bearing group." The process described by Robinson uses a reducing agent conforming to the formula "$R_2AlH$, where R is an alkyl radical." The reducing agent is diluted in a solvent and the process is run at atmospheric pressure.

Schulz, Co-pending U.S. Application 07/516,599, filed June 1, 1980 describes a process for reducing organohalosilanes and volatile organohalopolysilanes with liquid alkylaluminum hydride. The Co-pending Schulz application does not describe the reduction of silacycloalkanes. The reactive nature of the silacycloalkane ring makes these materials unique in relation to the organohalosilanes and volatile organohalopolysilanes described in the Co-pending Schulz patent application, and cited prior publications.

BRIEF SUMMARY OF INVENTION

The instant invention is a process for the production of silacycloalkanes. The described process employs an alkylaluminum hydride to reduce a halosilacycloalkane to a silacycloalkane reduced in halogen content. In a preferred embodiment of the instant invention, the halosilacycloalkane is added to the alkylaluminum hydride under temperature and pressure conditions that cause the silacycloalkane to vaporize immediately after it is formed. This allows the silacycloalkane product to be vacuum distilled from the resultant mixture immediately upon formation, virtually eliminating the occurrence of further reactions of the desired silacycloalkane. Thus, improved yields of product are achieved by the described process.

DESCRIPTION OF INVENTION

The instant invention is a process for producing silacycloalkanes of the formula

$$RHSiC_nH_{2n};$$

where R is selected from a group consisting of hydrogen and hydrocarbon radicals of one to ten carbon atoms; and $n=3$ to 8. The process comprises contacting a halosilacycloalkane of the formula

$$R_aX_{2-a}SiC_nH_{2n};$$

where n is as previously described; R is a hydrocarbon radical of one to ten carbon atoms; $a=0$ or 1; and X is a halogen; with an alkylaluminum hydride of formula

$$R'_bAlH_{3-b};$$

where R' is an independently selected alkyl group of 1 to 10 carbon atoms and $b=1$ or 2; to form a mixture.

In one embodiment of the instant invention, the process is run at about atmospheric pressure and within a temperature range of minus 80° C. to 30° C. In a second embodiment of the instant invention, the halosilacycloalkane is introduced below the surface of the alkylaluminum hydride to form a mixture. This process is run within a temperature range of 0° C. to 60° C., at a pressure sufficiently reduced to cause vaporization of the product silacycloalkane immediately after it is formed. The vaporized product is immediately removed from the reaction vessel by vacuum distillation.

The silacycloalkanes which can be formed by the process of the instant invention are reduced in the number of halogen atoms bound to the silicon atom. Where the halosilacycloalkane initially has two halogen atoms bound to the silicon atom, $a=0$, it may be possible to recover a product with only one of the halogen atoms removed.

The number of carbons incorporated in the silacycloalkane ring can vary from 3 to 8. The silacycloalkane can be, for example, silacyclobutane, silacyclopentane, silacyclohexane, silacycloheptane, and silacyclononane. The silicon atom of the silacycloalkane can be substituted with a hydrocarbon radical, R, of ten or less carbon atoms. The hydrocarbon radial can be, for example, an alkyl, cycloalkyl, alkenyl, aryl, or aralkyl. The hydrocarbon radical could be for example methyl, ethyl, n-propyl, phenyl, or tolyl.

One or more carbon atoms of the silacycloalkane ring may be substituted with one or more radicals independently selected from the group consisting of trialkylsilyl, alkyl, alkenyl, aryl, and aralkyl., and radicals of formula $R^oO—$, where $R^o$ is an alkyl or alkenyl radical of one to 10 carbon atoms, or an aryl radical. $R^o$ can be, for example, a methyl, ethyl, or phenyl radical. Mixtures of silacycloalkanes may be formed by the described process.

The silacycloalkanes are formed from the corresponding 1-halo-1-silacycloalkane, herein denoted as halosilacycloalkane. The halogen constituent can be chloride, fluoride, bromide, iodide atoms, or a combination thereof. The halosilacycloalkane can be, for example, 1,1-dichloro-1-silacyclobutane, 1,1-dichloro-1-silacycloheptane, 1,1-dichloro-1-silacyclooctane, 1,1-dibromo-1-silacyclobutane, 1-bromo-1-chloro-1-silacyclobutane, 1,1-difluoro-1-silacyclobutane, 1-methyl-1-chlorosilacyclobutane, 1-ethyl-1-chlorosilacyclobutane, 1-phenyl-1-chlorosilacyclobutane, 1-methyl-1-chlorosilacycloheptane, 1-methyl-1-bromosilacyclobutane.

The preferred halogen constituent is chloride and bromide atoms. Most preferred are chloride atoms. The preferred halosilacycloalkanes are 1,1-dichloro-1-silacyclobutane and 1,1-dibromo-1-silacyclobutane. Most preferred is 1,1-dichloro 1-silacyclobutane.

The halosilacycloalkane is contacted with an alkylaluminum hydride of formula $R_bAlH_{b-3}$, where R is an independently selected alkyl group of one to ten carbon atoms and where b is equal to one or two. The alkylaluminum hydride can be, for example, diethylaluminum hydride, dipropylaluminum hydride, diisoamylaluminum hydride, or diisobutylaluminum hydride. Preferred, is diisobutylaluminum hydride.

In one embodiment of the instant invention, the alkylaluminum hydride is contacted with the halosilacycloalkane at a mixture temperature in the range of minus 80° C. to 30° C. and at about atmospheric pressure. The lower end of the temperature range is determined primarily by the freezing point of the mixture of reactants and solvent. Depending upon the freezing point of the solvent, if employed, the reaction may be run at temperatures even lower than minus 80° C. When the process is run without solvent, the lower end of the temperature range is determined primarily by the alkylaluminum hydride freezing point. Temperatures greater than 30° C. may be employed, but typically result in reduced yield of product. The preferred temperature range for conducting the reaction is minus 80° C. to 0° C.

By about atmospheric pressure is meant, a pressure in the reaction vessel that is within 90 percent of the standard atmospheric pressure of 760 torr.

The alkylaluminum hydride is added to the halosilacycloalkane in a stoichiometric equivalent amount or in a slightly greater than stoichiometric equivalent amount of hydride to halide. By slightly greater than a stiochiometric equivalent amount is meant, that up to 40% mole percent excess of hydrogen as hydride may be added in relation to the number of moles of halogen to be displaced from the halosilacycloalkane. Preferred is a five to 20 mole percent excess of hydrogen as hydride, in relation to the halide.

It is preferred that the alkylaluminum hydride be added to the halosilacycloalkane. Although the halosilacycloalkane may be added to the alkylaluminum hydride, the high concentration of reducing agent can result in unwanted reactions. The rate of addition of the alkylaluminum hydride to the halosilacycloalkane is not critical. However, the reaction is somewhat exothermic. Therefore, the alkylaluminum hydride should be added to the halosilacycloalkane at a rate slow enough to avoid excessive heating of the mixture.

To maintain the desired temperature, the reaction vessel should be encompassed by a cooling means, for example, an ice water bath or a dry ice and solvent bath. The mixture should be agitated during addition of the alkylaluminum hydride both to prevent localized heating and to prevent localized concentrations of product in the mixture. Standard mixing apparatus such as a magnetic stirrer and stirring bar or a shaft and propeller type arrangement may be used.

No solvent is required in the reaction as described. The absence of solvent can greatly simplify separation of product from the product mixture. However, if desired, an inert, high boiling, organic solvent such as hexane, heptane, toluene, benzene, or tetrahydrofuran may be employed without reducing the effectiveness of the process. The solvent may be used to dilute the alkylaluminum hydride prior to addition to the reaction and to dilute the halosilacycloalkane before or during the process.

In a second embodiment of the instant invention, a quantity of alkylaluminum hydride is placed within a sealed vessel. A halosilacycloalkane is introduced at a controlled rate below the surface of the alkylaluminum hydride. The halosilacycloalkane can be delivered below the surface of the alkylaluminum hydride by, for example, a tube extending beneath the surface of the alkylaluminum hydride or a submerged port opening into the vessel. The advantage of delivering the halosilacycloalkane below the surface of the alkylaluminum hydride is to assure adequate contact time for the desired reduction to occur. Reduction of the halosilacycloalkane occurs before it can exit the alkylaluminum hydride as a gas.

During the addition step, the temperature of the mixture is maintained within a range of 0 to 60° C. and the pressure within the vessel is sufficiently reduced to cause vaporization of the product silacycloalkane from the mixture immediately after it is formed. The silacycloalkane vapor is immediately removed from the vessel by vacuum. The removed silacycloalkane can be condensed by, for example, a cold trap at minus 196° C. Alternatively, the removed silacycloalkane can be used as a direct feed to another process.

It is preferred that a slight excess of alkylaluminum hydride be added to the vessel, in relation to the total amount of halosilacycloalkane to be reduced. By slight excess is meant, up to 40 mole percent excess of hydrogen as hydride in relation to the amount of halogen to be displaced. The preferred range is 5 to 20 mole percent excess of hydrogen as hydride to halogen. Lessor amounts of alkylaluminum hydride can be used, but this will result in less than complete conversion of the halosilacycloalkane.

The rate of addition of the halosilacycloalkane to the alkylaluminum hydride is controlled. The optimum rate of addition depends on such factors as reactor size, stirring efficiency, and the ability to dissipate the heat of reaction and maintain the mixture at the desired temperature. The vessel may be cooled and stirred, for example, by previously described means. A useful rate for halosilacycloalkane addition has been found to be in the range of 0.5 ml to 3.0 ml per minute, for a 250 to 500 ml vessel.

The reaction is run under mixture temperature and vessel pressure conditions at which the resultant silacycloalkane is volatile. A workable range for mixture temperature is 0° C. to 60° C., with a corresponding vessel pressure of 0.1 to 200 torr. Preferred conditions are where the temperature of the mixture is 25° C. to 45° C., and the vessel pressure is 1.0 to 100 torr. Most preferred, is when the mixture temperature is about 30° C. and the vessel pressure is about 1 torr. The use of the term "about" in relation to the preferred temperature and pressure, is meant to indicate that slight variations in these parameters are permissible as long as product yield is not significantly impacted.

The process may be run with or without a high boiling solvent, as previously described. An advantage of running the process without solvent is that the spent reducing agent, alkylaluminum halide, can be recycled without additional separation steps.

The present processes describe a class of reducing agents, alkylaluminum hydride, for removing halogen from halosilacycloalkanes. The alkylaluminum hydrides offer the benefit of high reduction of the silicon-halogen bond, with lessor reaction of the silacycloalkane ring. In addition, a process is described in which a halosilacycloalkane is delivered below the surface of an excess of alkylaluminum hydride. The temperature and pressure of the process are maintained such that the reduced product immediately vaporizes and is removed from the vessel. This process results improved yields of desired product.

So that those skilled in the art may better understand and appreciate the instant invention, the following examples are presented. These examples are presented to be illustrative and are not to be construed as limiting the claims as delineated herein.

EXAMPLE 1

A number of metal hydride compounds were evaluated for their ability to convert 1,1-dichloro-1-silacyclobutane (DCSCB), hereafter referred to as dichlorosilacyclobutane, to silacyclobutane (SCB). A three-neck round-bottom flask of 250 to 500 ml capacity was employed as a reaction vessel. The flask was fitted with a thermometer, a sealed inlet port, and a water cooled condenser connected to a cold trap. The contents of the vessel were stirred by means of a magnetic stirrer. Temperature of the mixture was controlled by means of a cooling bath around the reaction vessel. Product was recovered from the vessel by vacuum distillation and trapping the resultant distillate in a cold trap maintained at minus 78° C. For a typical run, the experimental apparatus was flushed and maintained under a nitrogen atmosphere. The DCSCB was added to the reaction flask. The metal hydride compound was then added dropwise to the DCSCB over a period of time sufficient to prevent an excessive temperature rise, less than 30° C. At the completion of vacuum distillation, the contents of the cold trap were evaluated by gas chromatography utilizing a mass spectrometer (GC/MS).

The results of these evaluations are presented in Table 1. The headings of Table 1 are as follows: "Run No." references the specific procedure; "DCSCB" refers to the amount of dichlorosilacyclobutane added to the reaction vessel in moles (mol); "Metal Hydride" denotes the specific metal hydride added to the reaction in terms of moles (mol) of compound; "Temp." refers to the temperature in degrees centigrade (°C.) at which the reaction mixture was maintained during addition of the metal hydride; and the term "Yield" refers to the mole percent of added DCSCB recovered as silacyclobutane.

TABLE 1

Effect of Selected Metal Hydrides on Conversion of Dichlorosilacyclobutane to Silacyclobutane

| Run No. | DCSCB (mol) | Metal Hydride (Type) | (mol) | Temp. (°C.) | Yield (%) |
| --- | --- | --- | --- | --- | --- |
| 1 | 0.14 | Vitride[a] | 0.17 | 0 | 31[b] |
| 2 | 0.50 | LiAlH$_4$ | 0.30 | 24 | 60 |
| 3 | 0.008 | Me$_3$SnH | 0.008 | 24 | 0 |
| 4 | 0.07 | NaBH$_4$ | 0.044 | 24 | 0 |
| 5 | 0.21 | NaAlH$_2$Et$_2$ | 0.23 | 24 | —[c] |
| 6 | 0.14 | DIBAH[d] | 0.32 | 0 | 46 |
| 7 | 0.14 | DIBAH | 0.32 | −78 | 85 |
| 8 | 0.54 | DIBAH | 1.20 | −78 | 80 |

[a]Vitride (Hexcel Corporation) NaAlH$_2$(OCH$_2$CH$_2$OCH$_3$)$_2$
[b]Mixture appeared to polymerize
[c]Mixture gelled
[d]DIBAH — diisobutylaluminum hydride The results demonstrate the effectiveness of diisobutylaluminum hydride (DIBAH) in reducing dichlorosilacyclobutane to silacyclobutane.

EXAMPLE 2

Using apparatus and procedures similar to that described in Example 1, the effect of temperature on the conversion of dichlorosilacyclobutane to silacyclobutane by diisobutylaluminum hydride was evaluated. The results are presented in Table 2. The headings of Table 2 are the same as previously described for Table 1.

TABLE 2

Effect of Temperature on Conversion of Dichlorosilacyclobutane to Silacyclobutane by Diisobutylaluminum Hydride

| Run No. | DCSCB (mol) | Metal Hydride (Type) | (mol) | Temp. (°C.) | Yield (%) |
| --- | --- | --- | --- | --- | --- |
| 9 | 0.11 | DIBAH | 0.32 | −78 | 66 |
| 10 | 0.12 | DIBAH | 0.32 | −28 | 44 |
| 11 | 0.12 | DIBAH | 0.32 | 0 | 66 |

The data suggest that the reaction is not particularly temperature sensitive.

EXAMPLE 3

A series of runs were made in which DIBAH was first added to the reaction vessel, vacuum was applied, and DCSCB was slowly added beneath the surface of the DIBAH. The experimental apparatus was similar to that described in Example 1. The DCSCB was added beneath the surface of the DIBAH by means of a Teflon tube inserted through the sealed inlet port of the reaction vessel; the tube extending to the bottom of the vessel. Prior to addition of the DCSCB, the vessel was purged with argon gas. With this process, the product silacyclobutane was removed from the vessel immediately after it was formed. The specific conditions and results of these runs are presented in Table 3. The headings of Table 3 are as previously described for Table 1, with the following additions: the term "Press." refers to the pressure maintained in the vessel during the addition of the DCSCB; and the term "Feed" refers to the rate at which DCSCB was added to the reaction vessel.

TABLE 3

Effect on Yield of Vacuum Distilling Silacyclobutane
From Reaction Mixture Immediately Upon Formation

| Run No. | DCSCB (mol) | DIBAH (mol) | Feed (ml/min) | Press. (Torr) | Temp. (°C.) | Yield (%) |
|---|---|---|---|---|---|---|
| 12 | 0.12 | 0.32 | 1.0 | 1 | 42 | 95 |
| 13 | 0.12 | 0.32 | 0.75 | 25 | 30 | 97 |
| 14 | 0.12 | 0.32 | 1.0 | 1 | 30 | 85 |
| 15 | 0.22 | 0.31 | 2.0 | 80 | 30 | 97 |

A comparison of the yields of silacyclobutane in Table 3 with the yields reported in Table 2 indicates that improved yields can be achieved when the silacyclobutane is vacuum distilled immediately after formation.

What is claimed is:

1. A process for preparing silacycloalkanes of the formula $$RHSiC_nH_{2n};$$

where R is selected from a group consisting of hydrogen and hydrocarbon radicals of one to ten carbon atoms; and n=3 to 8;
the process comprising:
contacting a halosilacycloalkane of the formula $$R_aX_{2-a}SiC_nH_{2n};$$

where n and R are as previously described; a=0 or 1; and X is a halogen; with an alkylaluminum hydride of formula $$R'_bAlH_{3-b};$$

where R' is an independently selected alkyl group of 1 to ten carbon atoms and b=1 or 2; at a reaction temperature within a range of minus 80° C. to 30° C.; and at about atmospheric pressure.

2. The process of claim 1, where the alkylaluminum hydride is selected from a group consisting of diethylaluminum hydride, dipropylaluminum hydride, diisoamylaluminum hydride, and diisobutylaluminum hydride.

3. The process of claim 1, where the reaction temperature is within a range of minus 80° C. to 0 °C.

4. The process of claim 1, where the halosilacycloalkane is selected from a group consisting of 1,1-dichloro-1silacyclobutane and 1,1-dibromo-1-silacyclobutane.

5. The process of claim 3, where the halosilacycloalkane is 1,1-dichloro-1-silacyclobutane and the alkylaluminum hydride is diisobutylaluminum hydride.

6. The process of claim 5, where 2.1 to 2.4 moles of diisobutylaluminum hydride is added per mole of 1,1-dichloro-1-silacyclobutane.

7. A process for preparing silacycloalkanes of the formula $$RHSiC_nH_{2n};$$

where R is selected from a group consisting of hydrogen and hydrocarbon radicals of one to ten carbon atoms; and n=3 to 8; the process comprising:
(A) delivering a halosilacycloalkane of the formula $$R_aX_{2-a}SiC_nH_{2n};$$

where n and R are as previously described; a=0 or 1; and X is a halogen; below the surface of a liquid alkylaluminum hydride of formula $$R'_bAlH_{3-b};$$

where R' is an independently selected alkyl group of 1 to 10 carbon atoms, and b=1 or 2; to form a mixture;
(B) maintaining the mixture temperature within a range of 0° C. to 60° C.; and
(C) vacuum distilling the silacycloalkane from the mixture as the silacycloalkane is formed.

8. The process of claim 7, where the vacuum distilling is effected at a pressure of one to 100 torr.

9. The process of claim 7, where the mixture temperature is maintained at 25° C. to 45° C. and the vacuum distilling is effected at a pressure of one to 100 torr.

10. The process of claim 7, where the alkylaluminum hydride is selected from a group consisting of diethylaluminum hydride, dipropylaluminum hydride, diisoamylaluminum hydride, and diisobutylaluminum hydride.

11. The process of claim 7, where the halosilacycloalkane is selected from a group consisting of 1,1-dichloro-1-silacyclobutane and 1,1-dibromo-1-silacyclobutane.

12. The process of claim 9, where the halosilacycloalkane is 1,1-dichloro-1-silacyclobutane and the alkylaluminum hydride is diisobutylaluminum hydride.

13. The process of claim 12, where the mixture temperature is maintained at about 30° C. and the vacuum distilling is effected at about one torr.

14. The process of claim 13, where 2.1 to 2.4 moles of diisobutylaluminum hydride is added per mole of 1,1-dichloro-1-silacyclobutane to be reduced.

15. The process of claim 7, where 2.1 to 2.4 moles of diisobutylaluminum hydride is added per mole of 1,1-dichloro-1-silacyclobutane to be reduced.

16. A process for preparing silacycloalkanes of the formula $$RHSiC_nH_{2n-y}^{R''_y};$$

where R is selected from a group consisting of hydrogen and hydrocarbon radicals of one to ten carbon atoms; R'' is independently selected from the group consisting of trialkylsilyl, alkyl, alkenyl, aryl, aralkyl, and R°O-radicals; n=3 to 8; and y is an integer of 1 to 2n;
the process comprising:
contacting a halosilacycloalkane of the formula $$R_aX_{2-a}SiC_nH_{2n-y}^{R''_y};$$

where R, R'', and y are as previously described; a=0 or 1; and X is a halogen; with an alkylaluminum hydride of formula $$R'_bAlH_{3-b};$$

where R' is an independently selected alkyl group of 1 to ten carbon atoms, and b=1 or 2; at a reaction temperature within a range of minus 80° C. to 30° C.; and at about atmospheric pressure.

17. A process according to claim 16, where the alkylaluminum hydride is diisobutylaluminum hydride.

18. A process according to claim 17, where R" is independently selected from the group consisting of trimethylsilyl and methyl radicals.

19. A process according to claim 18, where y=1, 2, or 3.

20. A process for preparing silacycloalkanes of the formula $$RHSiC_nH_{2n-y}^{R''_y};$$

where R is selected from a group consisting of hydrogen and hydrocarbon radicals of one to ten carbon atoms; R" is independently selected from the group consisting of trialkylsilyl, alkyl, alkenyl, aryl, aralkyl, and R°O-radicals; n=3 to 8; and y is an integer of 1 to 2n;

the process comprising:

(A) delivering a halosilacycloalkane of the formula $$R_aX_{2-a}SiC_nH_{2n-y}^{R''_y};$$

where R, R", n, and y are as previously described; a=0 or 1; and X is a halogen; below the surface of a liquid alkylaluminum hydride of formula $$R'_bAlH_{3-b};$$

where R' is an independently selected alkyl group of 1 to 10 carbon atoms; and b=1 or 2; to form a mixture;

(B) maintaining the mixture temperature within a range of 0° C. to 60° C.; and (C) vacuum distilling the silacycloalkane from the mixture as the silacycloalkane is formed.

21. A process according to claim 20, where the alkylaluminum hydride is diisobutylaluminum hydride.

22. A process according to claim 21, where R" is independently selected from the group consisting of trimethylsilyl and methyl radicals.

23. A process according to claim 22, where y=1, 2, or 3.

* * * * *